United States Patent [19]

Motola et al.

[11] Patent Number: 4,580,978
[45] Date of Patent: Apr. 8, 1986

[54] DENTAL HIGH VOLUME EVACUATION SYSTEM

[76] Inventors: Vincent Motola, 317-88th St., Brooklyn, N.Y. 11209; Rudolph Vetere, 49 Sheraden Ave., Staten Island, N.Y. 10314

[21] Appl. No.: 582,094

[22] Filed: Feb. 21, 1984

[51] Int. Cl.⁴ ............................................. A61C 17/04
[52] U.S. Cl. ....................................... 433/92; 433/95; 604/73
[58] Field of Search ............................ 433/95, 91, 92; 128/277, 278, 276; 137/800

[56] References Cited

U.S. PATENT DOCUMENTS

| | | | |
|---|---|---|---|
| 1,353,587 | 9/1920 | Heck | 433/92 |
| 2,895,220 | 7/1959 | Johnston et al. | 433/92 |
| 3,051,175 | 8/1962 | Nugent | 433/92 X |
| 3,484,941 | 12/1969 | Svärd | 433/92 |
| 3,657,819 | 4/1972 | Söderqvist | 433/92 |
| 3,847,573 | 11/1974 | Gandrud | 433/92 X |
| 3,988,134 | 10/1976 | Gandrud | 433/92 X |
| 4,293,300 | 10/1981 | Cattani | 433/92 |
| 4,332,560 | 6/1982 | Rait | 433/95 |
| 4,344,756 | 8/1982 | Folkenroth et al. | 433/92 |
| 4,385,891 | 5/1983 | Ligotti | 433/92 |

FOREIGN PATENT DOCUMENTS 2038975 2/1972 Fed. Rep. of Germany ........ 433/92

*Primary Examiner*—Gene Mancene
*Assistant Examiner*—James Hakomaki
*Attorney, Agent, or Firm*—Collard, Roe & Galgano

[57] ABSTRACT

A vacuum operated dental high volume evacuation system is provided wherein an extraction instrument is connected to a debris collector for solids which in turn is connected to a separator unit wherein the liquid in the evacuated material is separated from the vacuum air and the dry vacuum air is directed to the vacuum source unit which creates the vacuum for the system. The separator unit includes a vacuum chamber positioned above a drainage chamber with a valve disposed therebetween. The drainage chamber is normally maintained at atmospheric pressure and the valve is normally closed due to the pressure differential between the two chambers. A liquid level sensor is provided in the vacuum chamber to sense the rise of liquid therein which upon reaching a certain level trips the sensor which results in an equalization of vacuum pressure between the two chambers and the draining of the liquid in the vacuum chamber into the drainage chamber. Upon the deactivation of the liquid level sensor, the drainage chamber is returned to atmospheric pressure and the valve between the two chambers closed as a result of the pressure differential.

11 Claims, 6 Drawing Figures

DENTAL HIGH VOLUME EVACUATION SYSTEM

The present invention relates to a high volume evacuation system for use by dentists in extracting the liquid and dental debris from the mouths of dental patients during dental procedures. More particularly, the present invention relates to such a system wherein vacuum is utilized to extract the liquid and debris from the patient's mouth or from other sources and transport the same first to a debris collector where the solid debris is separated from the liquid and the liquid and evacuated air are then transported to a separator unit where the liquid is separated from the vacuum air which then exhausts through the vacuum motor.

Heretofore, vacuum systems which have been utilized in extracting the liquid and debris from a dental patient's mouth or from another source during a dental procedure have basically consisted of so-called wet systems or dry systems. In the wet system vacuum apparatus, running water is utilized to establish a vacuum which is directed to the place to be evacuated such as the patient's mouth and which extracts the liquid and dental debris therefrom and transports it to the vacuum source which, in this case, is the continually running water. A significant disadvanatge of such a system is that a very large amount of water must be utilized during the continuous operation of the system which must then be discarded. Since the water which operates the system must be discarded during its use and may contain deleterious matter in the form of dental debris, significant environmental problems may arise. Obviously, one such environmental problem is the high rate of water usage during operation.

There are two types of dry systems being utilized. One employs turbines for establishing a vacuum to extract the liquid and dental debris and the other utilizes centrifugal vacuum pumps for establishing the vacuum. A major drawback for both of these systems is that each employs a debris canister wherein the extracted debris is collected during operation. Such a debris canister must periodically be emptied and, therefore, the system must be shut down at that time. This sometimes presents problems when the canister must be emptied while the dentist is performing a dental procedure on a patient.

A variant of the above described wet system utilizes an intermittent flow of liquid or water to extract the dental debris and liquid from a vacuum system. Such a system is described in U.S. Pat. No. 3,051,175, to Nugent, granted Aug. 28, 1962. In this system, a vacuum motor generates a vacuum which extracts the liquid and dental debris through a pipe connected to an aspirator nozzle in the patient's mouth. The liquid and dental debris are transported to a container where the solid debris and liquid are separated from the vacuum air which is then returned to the vacuum motor. This separation is accomplished by submerging the pipe returning from the patient's mouth in a liquid reservoir in the container and creating a vacuum above the liquid reservoir so that the wet vacuum air returning from the pipe is forced through the liquid so that dry vacuum air is returned to the vacuum source. In order to drain the container of the excess liquid and the dental debris accumulated, a float level switch is provided which operates a solenoid valve in a fluid line which, upon activation, permits fluid to flow therethrough and through an aspirating chamber which is connected to the bottom of the container. This flow of liquid creates a vacuum in the aspirating chamber which is greater than the vacuum utilized to evacuate the patient's mouth thereby drawing off the excess liquid in the container and the dental debris contained therein. This liquid and dental debris is then discarded together with the running water which creates the vacuum. Although this is a continually operating system without the need for shut down, there are still the environmental problems associated with the discarding of the dental debris and the water utilized for evacuating the debris.

Another problem which has been encountered by dentists when performing dental procedures on their patients has been associated with the vacuum source which is provided for creating the vacuum for saliva extraction. When vacuum motors are utilized as in the dry systems described above, there is the ever present danger that the motor providing the vacuum will fail at a crucial time during the dental procedure. In such an event, it is necessary for the dentist to halt his procedure and attend to the malfunctioning motor. Such a situation may be extremely detrimental to the dental procedure which the patient is undergoing.

It is, therefore, a primary object of the present invention to provide a vacuum operated dental high volume evacuation system which continually operates as desired without the need of running water for providing the vacuum source and which automatically discharges the dental debris and extracted liquids from the system.

According to the present invention, this object, as well as others which will hereinafter become apparent, is accomplished by providing a vacuum operated high volume evacuation system wherein the vacuum is generated by means of a series of sequentially operating motors which establish a vacuum at a place to be evacuated, such as an aspirator nozzle positioned in the patient's mouth. The extracted liquid and dental debris is directed first to a debris collector where the solid dental debris is separated from the mixture and then the wet vacuum (evacuated air and extracted liquid) is directed to a separator unit where the extracted liquid and any remaining dental debris are removed from the wet air vacuum and dry vacuum is then directed to the vacuum source. The separator unit includes two chambers, a vacuum chamber disposed above a discharge chamber and separated by means of a flap valve. The wet air vacuum enters the upper vacuum chamber where the liquid and dental debris separate from the wet vacuum and the dry vacuum is removed from the chamber to the vacuum source. As the liquid in the upper chamber rises, a liquid level sensor is activated to operate a first valve in the atmospheric vent of the discharge chamber to seal the chamber from the atmosphere. A second valve is also operated to equalize the vacuum in the upper and lower chambers thereby permitting the liquid in the upper chamber by means of its own weight to be exhausted into the lower chamber via the flap valve. When the liquid level in the upper chamber has dropped sufficiently, the liquid level sensor is deactivated so that the two chambers return to their normal operating pressures which in the case of the lower chamber is atmospheric pressure. Once the lower chamber has returned to atmospheric pressure, the liquid therein, because of its weight, is exhausted through a second flap valve to a collector or drain.

The present invention will be described and understood more readily when considered together with the accompanying drawings, in which.

Figure 1:
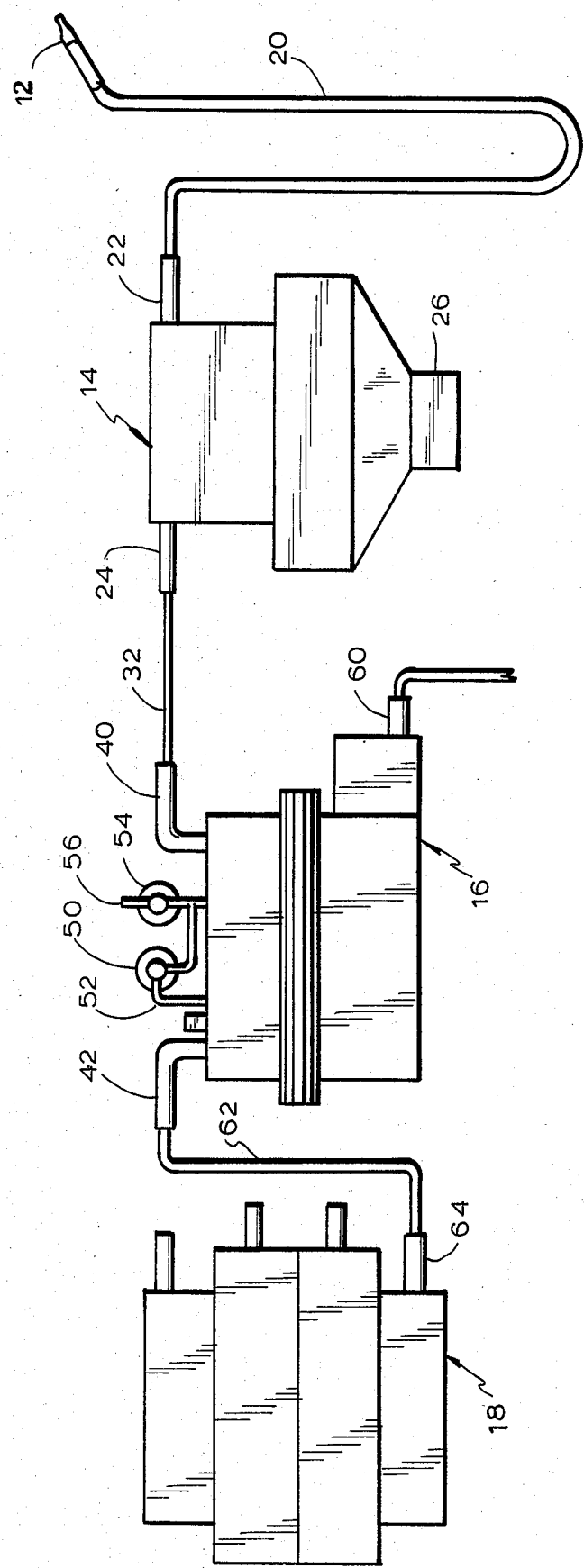
FIG. 1 is a schematic diagram of a dental high volume evacuation system according to the present invention.

Now turning to the drawings, there is shown in FIG. 1 a dental high volume evacuation system, generally designated 10, which includes an extraction instrument such as an aspirator nozzle, designated 12, a debris collector, designated 14, a separator unit, designated 16, and a vacuum source unit, designated 18. Aspirator nozzle 12 is generally positioned in the dental patient's mouth during a dental procedure for the purpose of extracting the liquid and dental debris which is produced during the dental procedure. Aspirator nozzle 12 is connected by means of a flexible hose, generally designated 20, to the inlet, designated 22, of debris collector 14. However, it is to be noted that aspirator nozzle 12 may be replaced by any instrument requiring vacuum for the removal of air, debris, water, blood, etc. Such instruments include, in addition to aspirators, saliva ejectors, high volume evacuators, cuspidor bowls, impression tray cooling hook ups, etc.

Figure 2:
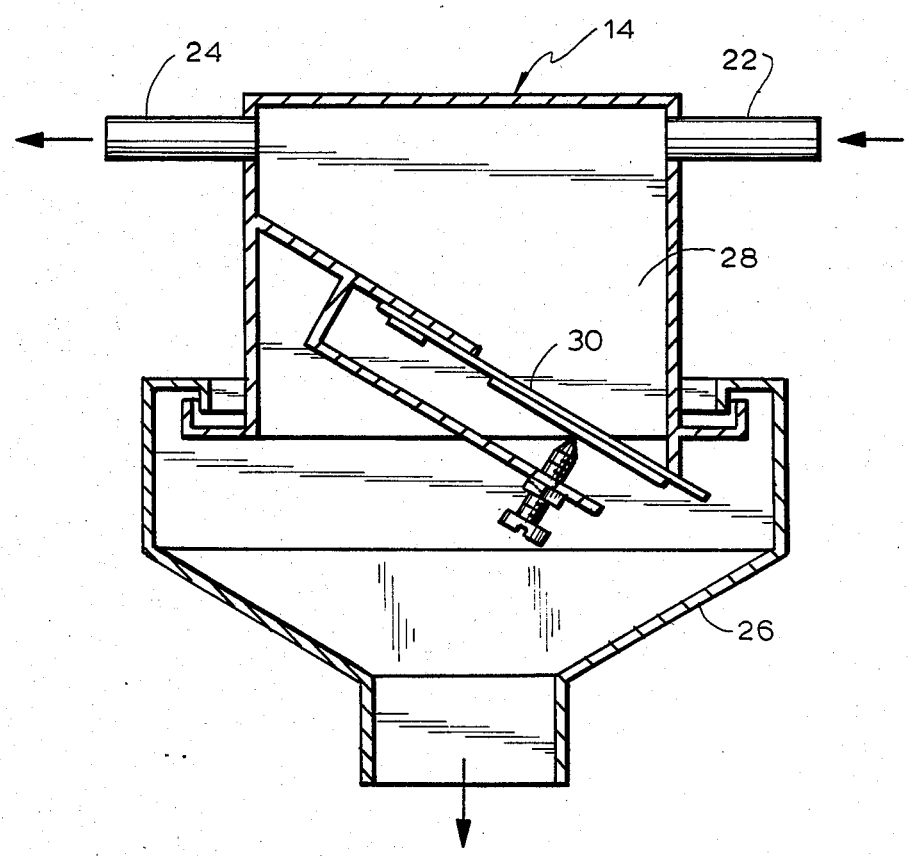
FIG. 2 is a cross-sectional view of the debris collector utilized in the system of the present invention.

Debris collector 14, as clearly seen in FIG. 2, is provided with an inlet 22 which communicates with aspirator nozzle 12, an outlet, designated 24, and a discharge chamber, generally designated 26. The purpose of debris collector 14 is to allow for the removal of solid dental debris which is removed from the dental patient's mouth by the nozzle aspirator. These solids are allowed to collect in the upper chamber, designated 28, of collector 14 which chamber is hermetically sealed from chamber 26. When the debris collected in chamber 28 reaches a sufficient level it is removed therefrom into discharge chamber 26 and discharged by means of gate 30. The wet vacuum air which enters collector 14 at inlet 22 is allowed to pass therethrough after deposition of the debris in collector 14 via outlet 24 which communicates with separator unit 16 by means of flexible hose 32.

Figure 3:
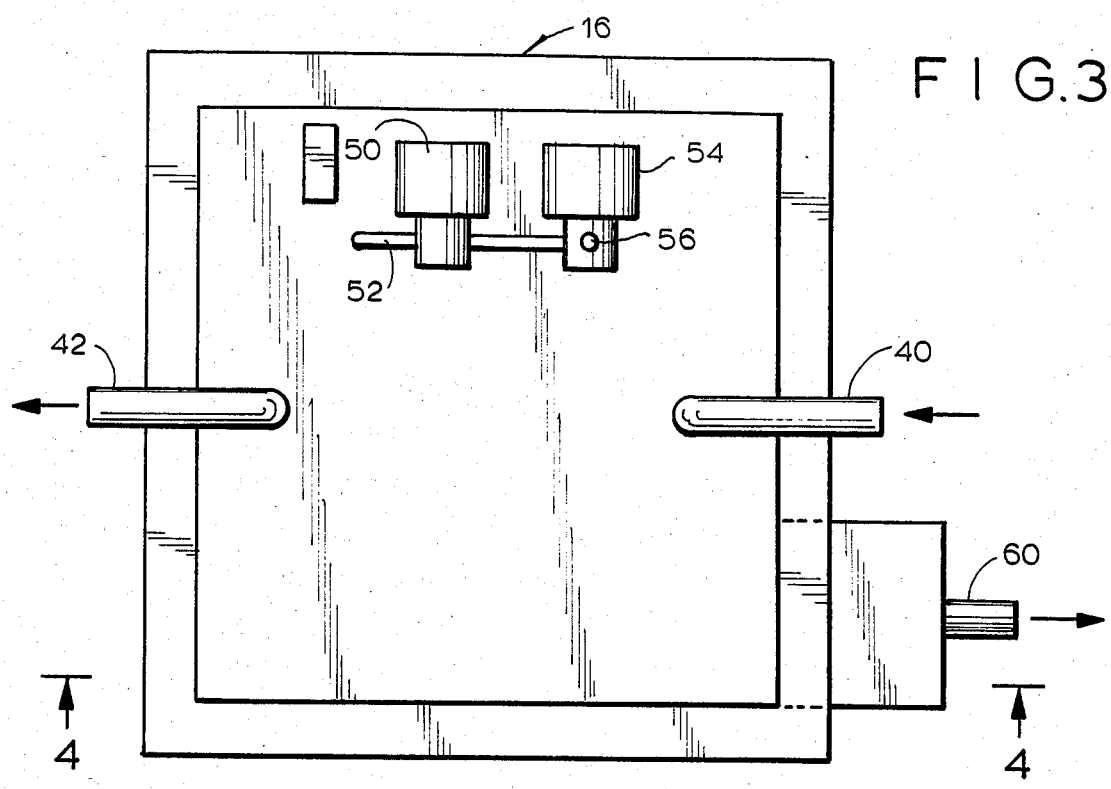
FIG. 3 is a top plan view of the separator unit utilized in the system of the present invention.
Figure 4:
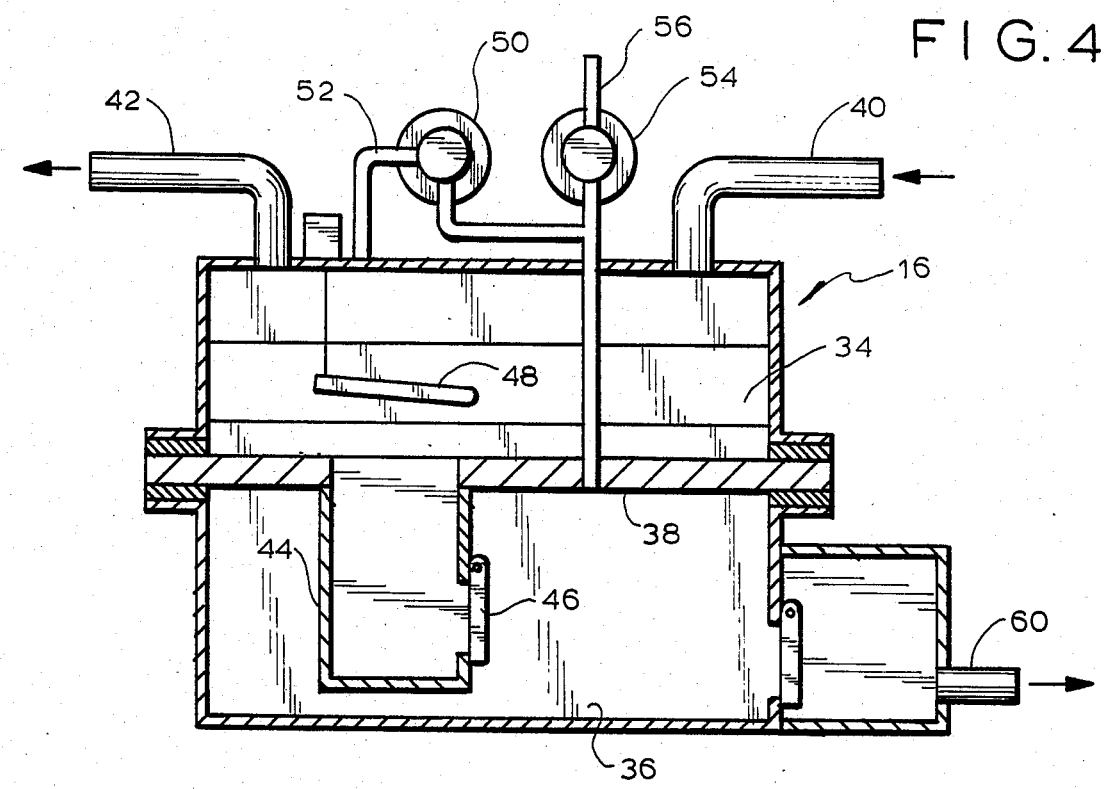
FIG. 4 is a cross-sectional view of the separator unit of FIG. 3 taken along the line 4—4 of FIG. 3.

As clearly seen in FIGS. 3 and 4, separator unit 16 includes an upper vacuum chamber, generally designated 34, and a lower drainage chamber, generally designated 36. Vacuum chamber 34 is separated from lower drainage chamber 36 by means of partition 38 and the two chambers are hermetically sealed from each other. Vacuum chamber 34 is provided with a vacuum inlet, designated 40, and a vacuum outlet, designated 42, which are arranged at the upper portion of the vacuum chamber. At the bottom of vacuum chamber 34 in partition 38, a liquid collector, generally designated 44, is arranged to communicate with vacuum chamber 34. At the lower portion of collector 44, is a one-way flap valve, generally designated 46, which is adapted to open into lower chamber 36. One-way valve 46 provides a hermetic seal between lower chamber 36 and upper vacuum chamber 34 when chamber 34 is at a lower pressure, such as a vacuum, than chamber 36. Vacuum chamber 34 additionally is provided with a liquid level sensor, generally designated 48, which is arranged to activate normally closed valve 50 in vacuum line 52 which connects vacuum chamber 34 with lower chamber 36. Liquid level sensor 48 is also adapted to activate normally open valve 54 which vents lower chamber 36 to the atmosphere through vent pipe 56. Valves 50 and 54 are preferably solenoid valves which are electrically controlled and easily activated by means of liquid level sensor 48. It is to be understood that flap valve 46 maintains the hermetic seal during pressure differential between the chambers even under the weight of liquid in chamber 34. Lower chamber 36 is provided with a one-way flap type drain valve, designated 58, which is adapted to hermetically seal lower chamber 36 when that chamber is at a lower pressure, i.e. vacuum, with respect to drain outlet 60 which is at atmospheric pressure.

Figure 5:
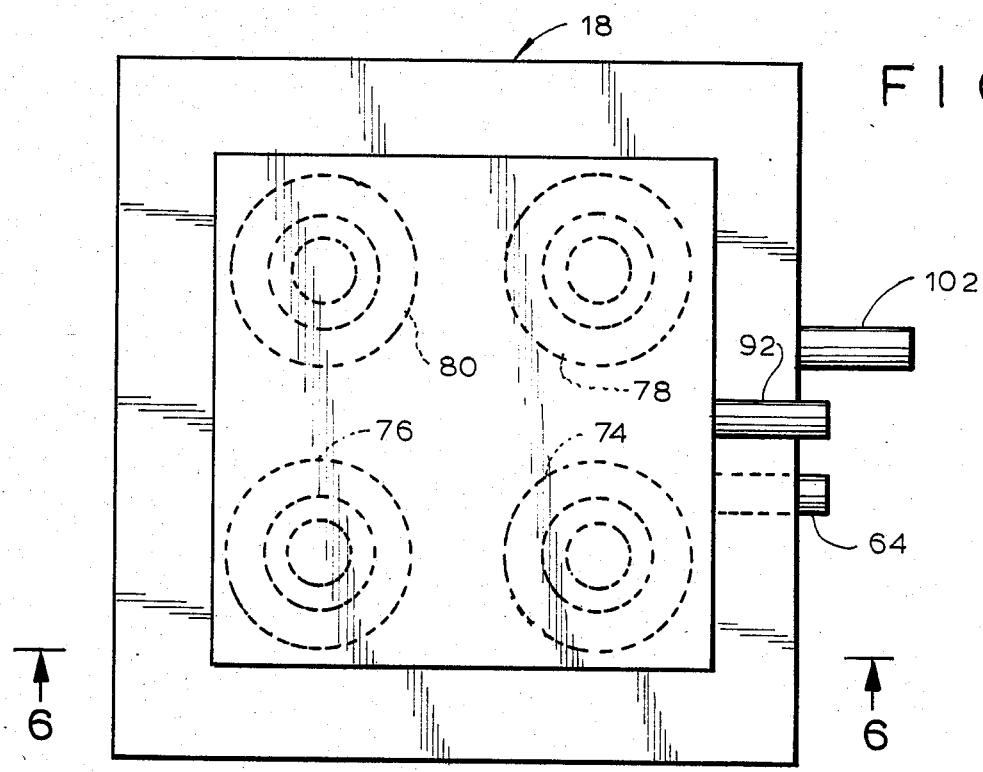
FIG. 5 is a top plan view of the vacuum source unit utilized in the system of the present invention.
Figure 6:
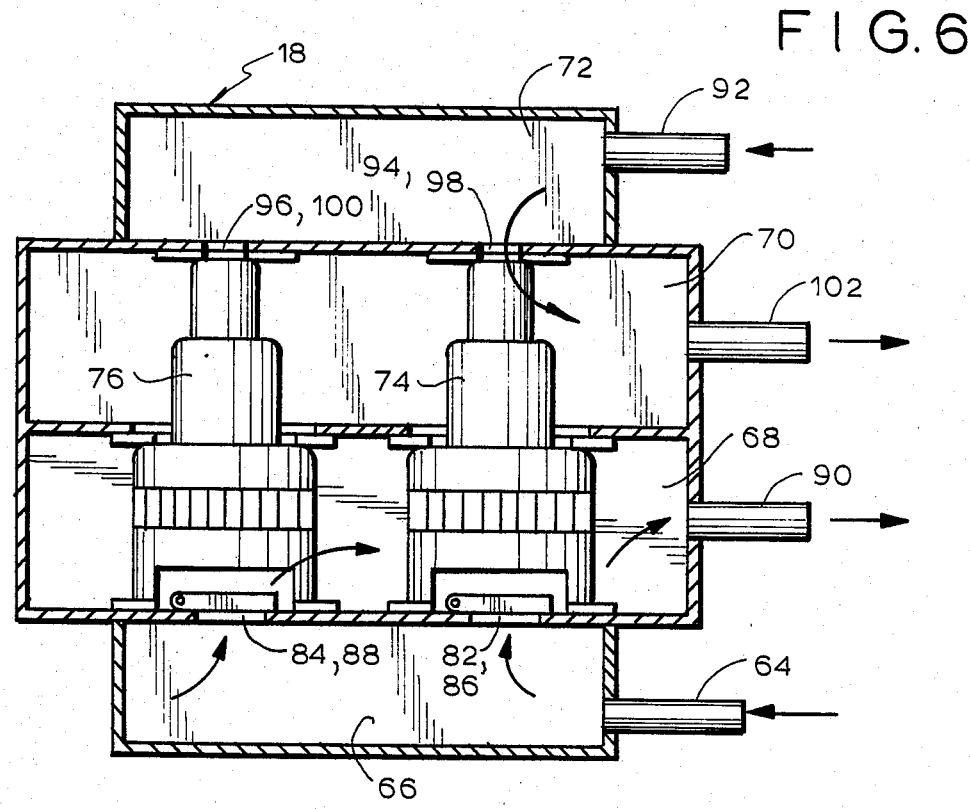
FIG. 6 is a cross-sectional view of the vacuum source unit according to FIG. 5 taken along the line 6—6 of FIG. 5.

Separator unit 16 is connected to vacuum source unit 18 by means of flexible hose 62 which is connected at unit 16 to vacuum outlet 42 and is connected to unit 18 at vacuum inlet 64. As clearly seen in FIGS. 5 and 6, vacuum source unit 18 includes a pyramid arrangement of four chambers, designated 66, 68, 70 and 72, respectively from one end thereof. As clearly seen in FIG. 6, chamber 66 of unit 18 is a vacuum chamber which communicates with separator unit 16 via vacuum inlet 64. Vacuum motors 74, 76, 78 and 80 communicate with vacuum chamber 66 by means of valves 82, 84, 86 and 88, respectively. Vacuum is drawn from chamber 66 into chamber 68 where it is exhausted through outlet 90. The vacuum motors are cooled by the drawing of cooling air through inlet 92 into chamber 72 and through the openings 94, 96, 98 and 100, respectively associated with each motor. The motors are cooled in chamber 70 and the cooling air exhausted at outlet 102.

In operation, when it is desired to perform a dental procedure on a patient, the aspirator nozzle 12 is positioned in the patient's mouth and the system turned on. When the system is turned on, one of the vacuum motors, for instance motor 74, is placed in operation to create a vacuum in vacuum chamber 66 and pass the evacuated air through open valve 82 through chamber 68 and out exhaust outlet 90. In this manner, a vacuum is created at aspirator nozzle 12 and the saliva and other liquids as well as dental debris within the patient's mouth are aspirated through the nozzle and into flexible hose 20 to debris collector 14. In debris collector 14, those solids which are present in the evacuated material are removed and the wet vacuum is passed through outlet 24 to separator unit 16. The vacuum which enters unit 16 through inlet 40 is termed a wet vacuum since it includes both evacuated air and liquid. In separator unit 16, the liquid is separated from the wet vacuum and accumulates in liquid collector 44 and the bottom of upper vacuum chamber 34. Since chamber 34 is exposed to a vacuum while lower chamber 36 is normally at atmospheric pressure because of the normally open valve 54 which vents the chamber through pipe 56, valve 46 hermetically seals chamber 34 from chamber 36. The dry vacuum exits from vacuum chamber 34 through vacuum outlet 42 and returns to vacuum chamber 66 of vacuum source unit 18. As the liquid in vacuum chamber 34 of separator unit 16 rises in liquid collector 44 and into chamber 34, liquid level sensor 48 is tripped by the rising liquid to activate valves 50 and 54. On activation, valve 54 closes thereby shutting off chamber 36 from the atmosphere and valve 50 opens to allow pressure equalization between chambers 34 and 36. When this occurs, the weight of liquid in chamber 34 causes valve 46 to open thereby draining chamber 34 into chamber 36. Inasmuch as chamber 36 is at a lower pressure than atmosphere, drain valve 58 therein is closed during this process. When the liquid level in chamber 34 drops sufficiently to deactivate liquid level sensor 48, valve 50 is closed and valve 54 is opened thereby returning chamber 36 to atmospheric pressure. The liquid in chamber 36 then causes drain valve 58 to open and the liquid is removed through drain outlet 60 to a suitable discharge.

Vacuum source unit 18, as noted, is provided with foru vacuum motors, each of which is connected to vacuum chamber 66 by its own respective valve which is normally closed when the associated motor is inoperative. It has been found that in order to provide continual operation of the dental saliva extractor system, these motors are preferably run sequentially for predetermined periods of time each so that the wear on the motors is evenly distributed. During the changeover between motors, it is necessary that the next motor to be sequentially operated be turned on automatically a predetermined time before the termination of operation of the previous motor. In the event that the next sequential motor to operate is for some reason incapable of operation, then an automatic arrangement can be provided so that the following motor operates in its stead. It is also possible, in the event the dental operator so chooses, to operate more than one motor during a dental procedure so that greater vacuum is thereby provided.

It is understood that the foregoing general and detailed descriptions are explanatory of the present invention and are not to be interpreted as restrictive of the scope of the following claims.

What is claimed is:

1. A dental high volume evacuation system for extracting liquid and dental debris by means of vacuum and automatically removing said extracted liquid and dental debris from said system, said system including:
   (a) a vacuum source;
   (b) an extraction instrument communicating with said vacuum source; and
   (c) a separator unit operatively disposed between said vacuum source and said extraction instrument for separating out the liquid extracted by said instrument from the evacuated air and automatically removing said extracted liquid from the system, said separator unit comprising,
   a vacuum chamber operatively disposed between and communicating with said extraction instrument and with said vacuum source,
   a drainage chamber disposed below said vacuum chamber for receiving the liquid from said vacuum chamber and draining said liquid from said system,
   valve means communicating between said vacuum and drainage chambers, and
   means responsive to the liquid level accumulated in said vacuum chamber for causing the opening of said valve means and the draining of the liquid from said vacuum chamber into said drainage chamber without altering the vacuum at said extraction instrument.

2. The dental high volume evacuation system as defined in claim 1, wherein said drainage chamber is normally vented at atmosphere and said means for causing the opening of said valve means and the draining of the liquid from said vacuum chamber into said drainage chamber includes:
   (a) a liquid level sensor activated by a predetermined liquid level in said vacuum chamber;
   (b) means responsive to the activation of said liquid level sensor for sealing the atmospheric vent of said drainage chamber; and
   (c) means responsive to the activation of said liquid level sensor for equalizing the pressures in said vacuum and drainage chambers.

3. The dental high volume evacuation system as defined in claim 2, wherein the valve means communicating between said vacuum and drainage chambers remains sealingly closed when a pressure difference exists between said chambers and is unrestrained when the pressures in said chambers are equalized thereby permitting the liquid in the vacuum chamber to drain into the drainage chamber by means of the weight of the liquid alone.

4. The dental high volume evacuation system as defined in claim 3, wherein the means for equalizing the pressures in said vacuum and drainage chambers includes means for pressure communication between said vacuum and drainage chambers and normally closed valve means in said pressure communication means responsive to the activation of said liquid level sensor to open thereupon and establish said pressure communication.

5. The dental high volume evacuation system as defined in claim 4, wherein said means for sealing the atmospheric vent of said drainage chamber includes a normally open valve means in said vent which closes in response to the activation of said liquid level sensor.

6. The dental high volume evacuation system as defined in claim 5, wherein said drainage chamber includes a valve means disposed therein for draining the liquid in said chamber therefrom, the valve means remains sealingly closed due to the pressure differential between said chamber and atmosphere when the valve means in the drainage chamber vent is closed and the valve means in the pressure communication means between the vacuum and drainage chambers is open, the valve means in said drainage chamber being unrestrained when the pressure in said chamber is equalized with atmospheric pressure thereby allowing the liquid therein to drain therefrom by means of the weight of the liquid alone.

7. The dental high volume evacuation system as defined in claim 1, which further includes a debris collector operatively disposed between said extraction instrument and said separator unit.

8. The dental high volume evacuation system as defined in claim 1, wherein said vacuum source includes a vacuum chamber operatively communicating with the vacuum chamber of said separator unit, at least one vacuum motor disposed exteriorly to said vacuum chamber of said vacuum source, and a valve associated with said at least one vacuum motor and said chamber which is open during operation of said at least one vacuum motor to create a vacuum in said vacuum chamber of said vacuum source.

9. The dental high volume evacuation system as defined in claim 8, wherein said vacuum source includes a plurality of vacuum motors each having an associated valve for communication with the vacuum chamber of said vacuum source and wherein said motors operate sequentially for predetermined time periods during operation of the dental high volume evacuation system.

10. The dental high volume evacuation system as defined in claim 9, wherein said vacuum source includes four vacuum motors.

11. The dental high volume evacuation system as defined in claim 9, wherein there is a time delay in the shutting off of each vacuum motor when the successive motor has started operating.

* * * * *